US00PP16787P2

(12) United States Plant Patent
Bolwijn

(10) Patent No.: US PP16,787 P2
(45) Date of Patent: Jul. 11, 2006

(54) ***EUONYMUS* PLANT NAMED 'GOLDBOLWI'**

(50) Latin Name: *Euonymus japonicus*
Varietal Denomination: Goldbolwi

(75) Inventor: Albert Leonard Christian Bolwijn, Putten (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 38 days.

(21) Appl. No.: 11/077,406

(22) Filed: Mar. 10, 2005

(51) Int. Cl.
*A01H 5/00* (2006.01)

(52) U.S. Cl. ..... Plt./246
(58) Field of Classification Search ..... Plt./246
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Euonymus* plant named 'Goldbolwi', characterized by its compact and upright plant habit; freely basally branching growth habit; and distinct yellow and green variegated leaves.

1 Drawing Sheet

Botanical designation: *Euonymus japonicus*.
Cultivar denomination: 'Goldbolwi'.

BACKGROUND OF THE INVENTION

The present Invention relates to a new and distinct cultivar of *Euonymus* plant, botanically known as *Euonymus japonicus*, and hereinafter referred to by the name 'Goldbolwi'.

The new *Euonymus* is a naturally-occurring branch mutation of the *Euonymus japonicus* cultivar China Gold, not patented. The new *Euonymus* was discovered and selected by the Inventor in a controlled environment in Putten, The Netherlands in 1996. The new *Euonymus* was selected on the basis of its unique leaf coloration.

Asexual reproduction of the new cultivar by cuttings since January, 1998 in Putten, The Netherlands, has shown that the unique features of this new *Euonymus* are stable and reproduced true to type in successive generations.

SUMMARY OF THE INVENTION

Plants of the cultivar Goldbolwi have not been observed under all possible environmental conditions. The phenotype may vary somewhat with variations in environment such as temperature and light intensity without, however, any variance in genotype.

The following traits have been repeatedly observed and are determined to be the unique characteristics of 'Goldbolwi'. These characteristics in combination distinguish 'Goldbolwi' as a new and distinct *Euonymus* cultivar:

1. Compact and upright plant habit.
2. Freely basally branching growth habit.
3. Distinct yellow and green variegated leaves.

Plants of the new *Euonymus* are most similar to plants of the parent, the cultivar China Gold. In side-by-side comparisons conducted in Putten, The Netherlands, plants of the new *Euonymus* differed from plants of the cultivar China Gold in the following characteristics:

1. Plants of the new *Euonymus* grew slower than plants of the cultivar China Gold.

2. Leaves of plants of the new *Euonymus* had larger areas of yellow-coloration than leaves of plants of the cultivar China Gold.

Plants of the new *Euonymus* can be compared to plants of the *Euonymus* cultivar Golden Maiden, not patented. In side-by-side comparisons conducted in Putten, The Netherlands, plants of the new *Euonymus* differed from plants of the cultivar Golden Maiden in the following characteristics:

1. Plants of the new *Euonymus* were larger than plants of the cultivar Golden Maiden.
2. Plants of the new *Euonymus* had shorter internodes than plants of the cultivar Golden Maiden.
3. Leaves of plants of the new *Euonymus* had larger areas of yellow-coloration than leaves of plants of the cultivar Golden Maiden.

Plants of the new *Euonymus* can also be compared to plants of the *Euonymus* cultivar Luna, not patented. In side-by-side comparisons conducted in Putten, The Netherlands, plants of the new *Euonymus* differed from plants of the cultivar Luna in the following characteristics:

1. Plants of the new *Euonymus* grew slower than plants of the cultivar Luna.
2. Plants of the new *Euonymus* had shorter internodes than plants of the cultivar Luna.
3. Leaves of plants of the new *Euonymus* had larger areas of yellow-coloration than leaves of plants of the cultivar Luna.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Euonymus*. The photograph comprises a side perspective view of a typical flowering plant of 'Goldbolwi' grown in a container.

DETAILED BOTANICAL DESCRIPTION

Plants shown in the aforementioned photograph and used in the following description were grown in containers under conditions which closely approximate commercial production conditions in a glass-covered greenhouse in Putten, The Netherlands. Plants in the photograph and those used for the description were about 1.5 years old when the photographs and description were taken. During the production of the plants, day temperatures ranged from 0 to 32° C. and night temperatures ranged from 0 to 18° C. In the following description, color references are made to The Royal Horticultural Society Colour Chart, 1995 Edition, except where general terms of ordinary dictionary significance are used.

Botanical classification: *Euonymus japonicus* cultivar Goldbolwi.

Parentage: Naturally-occurring branch mutation of the *Euonymus japonicus* cultivar China Gold, not patented.

Propagation:

*Type*.—By cuttings.

*Time to initiate rooting, summer*.—About 25 days at 20° C.

*Time to initiate rooting, winter*.—About 35 days at 13° C.

*Time to produce a rooted young plant, summer*.—About 75 days at 20° C.

*Time to produce a rooted young plant, winter*.—About 140 days at 13° C.

*Root description*.—Thick; creamy white in color.

*Rooting habit*.—Freely branching; dense.

Plant description:

*Plant and growth habit*.—Perennial. Compact and upright plant habit. Freely basal branching habit; about seven branches per plant with short internodes; dense and bushy plant habit.

*Growth rate*.—Relatively slow-growing; plants grow about 15 to 20 cm per year.

*Plant height*.—About 24 cm.

*Plant width*.—About 21 cm.

*Branch description*.—Length: About 24 cm. Diameter: About 3 mm. Internode length: About 8 to 12 mm. Strength: Strong. Texture: Smooth, glabrous. Color: 6B.

*Foliage description*.—Arrangement: Opposite, simple. Length: About 3.9 cm. Width: About 1.8 cm. Shape: Lanceolate. Apex: Acute. Base: Attenuate. Margin: Crenate. Texture, upper and lower surfaces: Smooth, glabrous. Venation pattern: Pinnate. Color: Developing foliage, upper surface: Central area, 6B; towards the margin, 143A. Developing foliage, lower surface: Central area, 10C; towards the margin, 138A. Fully expanded foliage, upper surface: Central area, 6B; towards the margin, 139A; venation, similar to lamina. Fully expanded foliage, lower surface: Central area, 10C; towards the margin, 146A; venation, similar to lamina. Petiole length: About 6 mm. Petiole diameter: About 1.5 mm. Petiole texture, upper and lower surfaces: Smooth, glabrous. Petiole color, upper and lower surfaces: 6B.

Flower description: Flower development on plants of the new *Euonymus* has not been observed.

Disease/pest resistance: Plants of the new *Euonymus* have not been noted to be resistant to pathogens and pests common to *Euonymus*.

Temperature tolerance: Plants of the new *Euonymus* have been observed to tolerate temperatures from −5 to of 30° C.

It is claimed:

1. A new and distinct cultivar of *Euonymus* plant named 'Goldbolwi', as illustrated and described.

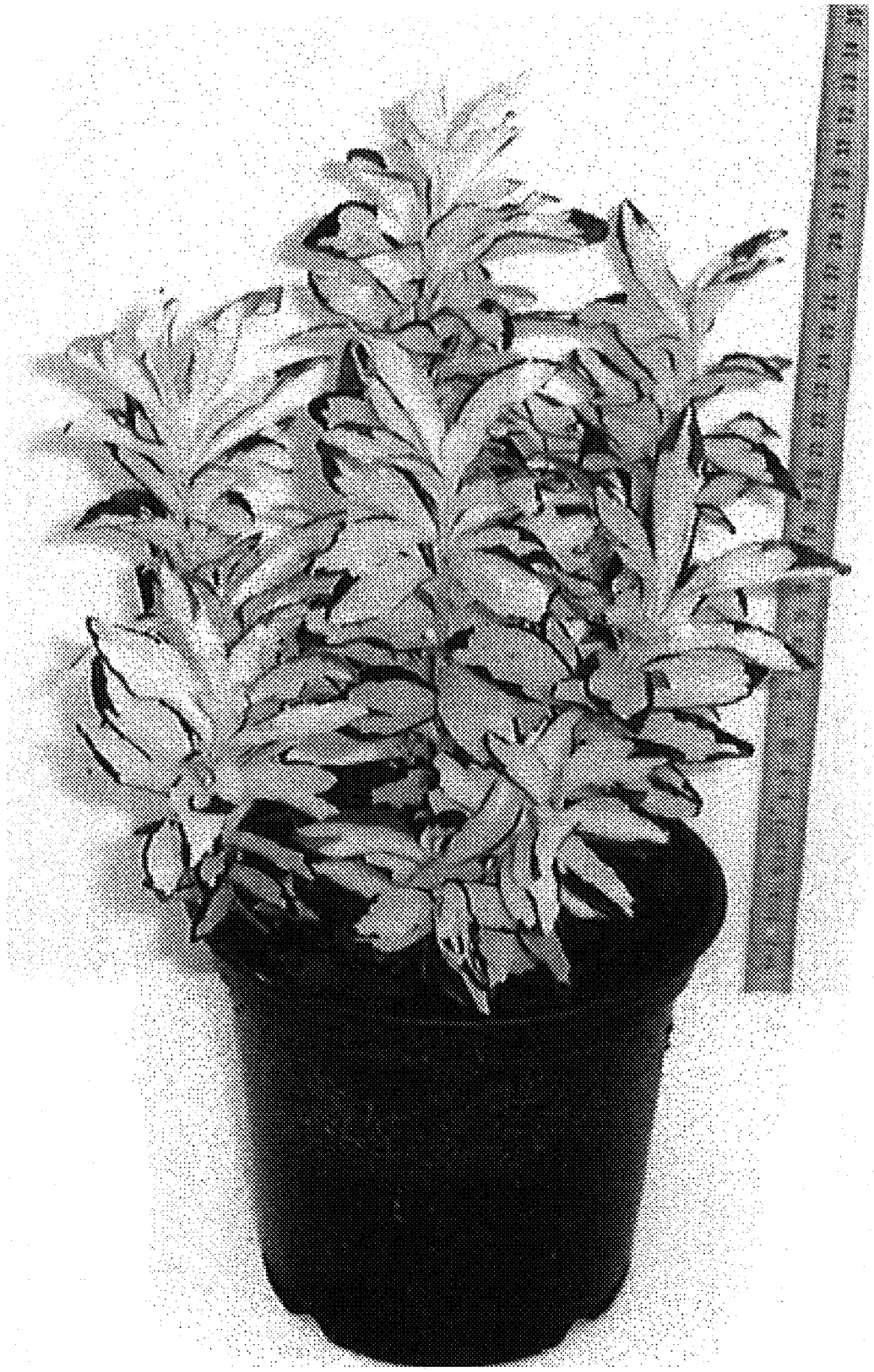

* * * * *